US011951953B2

(12) United States Patent
 Schadt (10) Patent No.: US 11,951,953 B2
(45) Date of Patent: Apr. 9, 2024

(54) VEHICLE

(71) Applicant: MERCEDES-BENZ GROUP AG, Stuttgart (DE)

(72) Inventor: Torsten Schadt, Böblingen (DE)

(73) Assignee: MERCEDES-BENZ GROUP AG, Stuttgart (DE)

( * ) Notice: Subject to any disclaimer, the term of this patent is extended or adjusted under 35 U.S.C. 154(b) by 0 days.

(21) Appl. No.: 18/265,488

(22) PCT Filed: Nov. 19, 2021

(86) PCT No.: PCT/EP2021/082360
§ 371 (c)(1),
(2) Date: Jun. 6, 2023

(87) PCT Pub. No.: WO2022/122349
PCT Pub. Date: Jun. 16, 2022

(65) Prior Publication Data
US 2023/0391294 A1    Dec. 7, 2023

(30) Foreign Application Priority Data

Dec. 7, 2020  (DE) ................. 10 2020 007 463.4

(51) Int. Cl.
*B60S 1/64* (2006.01)
*A61L 2/10* (2006.01)
(Continued)

(52) U.S. Cl.
CPC . *B60S 1/64* (2013.01); *A61L 2/10* (2013.01); *A61L 2/18* (2013.01); *A61L 2/20* (2013.01);
(Continued)

(58) Field of Classification Search
CPC ....................................................... B60S 1/64
See application file for complete search history.

(56) References Cited

U.S. PATENT DOCUMENTS

| 10,507,843 | B2 | 12/2019 | Abe et al. |
| 11,124,219 | B2 | 9/2021 | Hansen et al. |
| 2015/0329137 | A1 | 11/2015 | Onica |

FOREIGN PATENT DOCUMENTS

| CN | 109200305 A | 1/2019 |
| CN | 109318979 A | 2/2019 |

(Continued)

OTHER PUBLICATIONS

International Search Report and Written Opinion dated Mar. 3, 2022 in related/corresponding International Application No. PCT/EP2021/082360.

(Continued)

*Primary Examiner* — Jason Y Ko
(74) *Attorney, Agent, or Firm* — PATENT PORTFOLIO BUILDERS PLLC (57) ABSTRACT

A vehicle has a steering device with a manually actuatable steering input unit for manual gripping and inputting steering commands. The steering input unit has a one-piece or multi-piece gripping surface that is manually grippable for inputting steering commands, and a cleaning device for cleaning the gripping surface. The steering input unit is movable between a usage position, in which it can be gripped by the driver, and a non-usage position in which it cannot be gripped by the driver. The cleaning device has at least one cleaning box arranged on the vehicle and having or containing a cleaning device for cleaning the gripping surface. In the usage position the steering input unit is arranged outside the cleaning box at least in the region of the gripping surface and in the non-usage position it is arranged inside the cleaning box at least in the region of the gripping surface.

10 Claims, 4 Drawing Sheets

(51) Int. Cl.
- *A61L 2/18* (2006.01)
- *A61L 2/20* (2006.01)
- *A61L 2/26* (2006.01)
- *B08B 1/00* (2006.01)
- *B08B 1/02* (2006.01)
- *B08B 3/04* (2006.01)
- *B62D 1/183* (2006.01)
- *B62D 1/12* (2006.01)

(52) U.S. Cl.
CPC ............... *A61L 2/26* (2013.01); *B08B 1/008* (2013.01); *B08B 1/02* (2013.01); *B08B 3/04* (2013.01); *B62D 1/183* (2013.01); *A61L 2202/11* (2013.01); *A61L 2202/122* (2013.01); *A61L 2202/14* (2013.01); *A61L 2202/17* (2013.01); *B62D 1/12* (2013.01)

(56) References Cited

FOREIGN PATENT DOCUMENTS

| | | |
|---|---|---|
| CN | 208897149 U | 5/2019 |
| DE | 102013002539 A1 | 3/2014 |
| DE | 102014017616 A1 | 6/2016 |
| DE | 112015002234 T5 | 2/2017 |
| DE | 102017211515 A1 | 1/2019 |
| DE | 102018210924 A1 | 3/2019 |
| DE | 102019114717 A1 | 12/2019 |
| JP | H1178704 A | 3/1999 |
| JP | 2005225279 A | 8/2005 |
| JP | 2017206153 A | 11/2017 |
| JP | 2019006306 A | 1/2019 |
| KR | 20060112475 A | 11/2006 |
| WO | 2017060149 A1 | 4/2017 |

OTHER PUBLICATIONS

Office Action created Jul. 27, 2021 in related/corresponding DE Application No. 10 2020 007 463.4.

Notice of Reasons for Refusal dated Oct. 31, 2023 in related/corresponding JP Application No. 2023-534213.

VEHICLE

BACKGROUND AND SUMMARY OF THE INVENTION

Exemplary embodiments of the present invention relate to a vehicle.

For various reasons, it is necessary, in the case of a vehicle, to clean and in particular disinfect the gripping surface of the steering input unit. For example, there may be an increased hygiene requirement with regard to the spread or transfer of diseases. Likewise, the use of vehicles by various drivers, e.g., in a fleet or in car sharing, can increase the need for a cleaned gripping surface on the steering input unit.

A vehicle of the type in question is known, for example, from DE 10 2013 002 539 A1 and is equipped with a steering device for steering the vehicle, which has a manually operable steering input unit, e.g., in the form of a steering wheel, for manual gripping and inputting of steering commands, wherein the steering input unit has a one-piece or multi-piece gripping surface that can be manually gripped by the driver for inputting steering commands. The vehicle of the type in question is also equipped with a cleaning device for cleaning the gripping surface. In the known vehicle, the cleaning device comprises a housing, e.g., accommodated in the dashboard, in which a cleaning head of the cleaning device is accommodated. For a cleaning process, this cleaning head can now be folded or extended out of the housing, such that, for the cleaning operation, the cleaning head engages around a peripheral portion of the steering input unit designed as a steering wheel. A relative movement between the gripping surface and the cleaning head is achieved by a rotational movement of the steering wheel about its steering wheel axis, such that the gripping surface can be cleaned over the entire circumference of the steering wheel. The cleaning head is equipped with means for applying a fluid to the respectively gripped peripheral segment of the steering wheel, wherein the fluid contains a cleaning agent and/or disinfectant.

Furthermore, a cleaning surface for mechanical cleaning of the received peripheral portion and/or a radiation source for emitting electromagnetic radiation for killing germs and organisms can be provided in the cleaning head. In the known vehicle, the steering wheel, to be able to be cleaned, must be transferred from its current usage position, set by the respective driver, into a starting position in which the cleaning head can engage around the respective peripheral portion of the steering wheel. Thus, a comparatively complex synchronization of different devices is necessary in order to carry out the cleaning operation.

DE 10 2019 114 717 A1 discloses a vehicle having a manually operable steering input unit, and in particular a steering wheel, for manual gripping and input of steering commands. The steering wheel is hinged to a movable and collapsible steering wheel support arm and can thus be displaced between an extended usage position in which the input of steering commands is possible, and a retracted non-usage position. In the non-usage position, the steering wheel together with the steering wheel support arm is received in a receiving space arranged in an armrest.

DE 11 2015 002 234 T5 describes an air-conditioned steering wheel having a steering wheel rim, wherein at least the steering wheel rim is able to be heated or cooled.

The present invention addresses the problem of providing, for a vehicle of the type described above, an improved or at least another embodiment which is characterized in particular by an efficient cleaning of the gripping surface. Furthermore, reduced complexity is sought.

The invention is based upon the general concept of designing the steering input unit to be movable in such a way that it is arranged on the vehicle so as to be movable between an extended usage position, in which it can be gripped by the vehicle driver, and a retracted non-usage position, in which it cannot be gripped by the vehicle driver. Furthermore, it is proposed to equip the cleaning device with at least one cleaning box that is arranged on the vehicle and has or contains at least one cleaning device for cleaning the gripping surface. Furthermore, the movability of the steering input unit and the cleaning box are coordinated with one another such that the steering input unit is arranged, in the usage position, at least in the region of the gripping surface, outside the cleaning box, while, in the non-usage position, it is arranged inside the cleaning box, at least in the region of the gripping surface. The accommodation or positioning of the steering input unit in the non-usage position inside the cleaning box results in many advantageous possibilities for the design of the respective cleaning device. Since the entire gripping surface is arranged inside the cleaning box, liquid cleaning agents can be used, for example, without the risk that cleaning agents enter the vehicle interior in the process and cause contamination there. Furthermore, the invention makes use of the finding that, in the case of vehicles designed for autonomous driving, a steering input unit is frequently already provided, which can be moved from a usage position arranged within the vehicle interior into a non-usage position arranged outside the vehicle interior. For example, the steering input unit can be completely accommodated in the dashboard. In any case, it is also envisaged in such vehicles that the steering input unit no longer be able to be gripped by the vehicle driver in the respective non-usage position. If a receiving space for the steering input unit for such a non-usage position is now in any case provided in such vehicles, this receiving space, present in any case, can be configured or used as a cleaning box for implementing the invention presented here. Thus, synergies can be used here, as a result of which the complexity of the vehicle presented here having the cleaning device is reduced.

In this case, the gripping surface can, in particular, also comprise pushbuttons, switches, rockers, and the like.

The vehicle can in principle be any desired vehicle, i.e., in particular, a land vehicle, a watercraft, or an aircraft. It is preferably a road vehicle, and in particular a passenger car.

The steering input unit therefore, expediently, protrudes into a vehicle interior in the usage position. In an advantageous embodiment, the cleaning box can now be movable between an open state, in which the steering input unit is movable between the usage position and the non-usage position, and a closed state, in which the steering input unit moved into the non-usage position is separated from the vehicle interior. As a result of this separation of a box interior from the vehicle interior, the gripping surface on the steering input unit can be cleaned within the box interior, without disadvantageous interactions with the vehicle interior occurring. In particular, liquid and gaseous cleaning agents can thus be used, as well as irradiation.

In this case, the movement of the steering input unit can, in principle, occur in any suitable manner. A linear movement of the steering input unit is conceivable, for example. Simple or multiple pivoting or folding in of the steering input unit is also conceivable.

In order to be able to move the cleaning box between the open state and the closed state, it is conceivable to design the cleaning box in two parts, such that it has, for example, a box lower part and a box upper part that are movable relative to one another. It is also conceivable to equip the cleaning box with an opening to the vehicle interior, through which the steering input unit can be retracted into the cleaning box or can be extended therefrom. The cleaning box can then additionally be equipped with a cover for closing this opening. In particular, this cover can be inserted flush into the dashboard in the closed state.

The cleaning box can be equipped with a single cleaning device or with several cleaning devices. In the following, several different embodiments for such cleaning devices are presented, which can be used alternatively and together in any combination.

For example, such a cleaning device can be designed for mechanically cleaning the gripping surface. For this purpose, the cleaning device can have resilient cleaning elements, such as bristles, fingers, knobs, or a sponge. Mechanical cleaning using a fluid jet can also be realized wet or dry, i.e., using a liquid jet or a gas jet, for which purpose the respective fluid is applied to the gripping surface, for example, with an increased pressure. In particular, food residues and the like can thereby be removed particularly efficiently from the gripping surface.

It can, expediently, be provided that the same or another cleaning device be designed for generating a relative movement between the respective cleaning device and the gripping surface. This is advantageous, in particular, in conjunction with a cleaning device for mechanically cleaning the gripping surface. For example, the cleaning box can be moved relative to the stationary steering input unit. Oscillation movements, vibrations, or even bidirectional linear or rotating movements are conceivable. Additionally, or alternatively, the steering input unit can of course also be actuated for generating such relative movements. Furthermore, it is conceivable to apply a gas flow to the cleaning elements of the mechanically cleaning cleaning device, in order to move the cleaning elements, such as bristles, fingers, knobs, relative to the gripping surface. It is also conceivable that a nozzle which generates a fluid jet for mechanical cleaning be moved along the gripping surface.

In another embodiment, at least one such cleaning device can be designed to apply a cleaning liquid to the gripping surface, in order to effect a chemical cleaning of the gripping surface with the aid of the cleaning liquid. The cleaning liquid can contain, in particular, grease-dissolving components and/or disinfecting components. Furthermore, it can be provided that at least one such cleaning device have first cleaning elements for mechanically cleaning the gripping surface, and second cleaning elements for applying a cleaning liquid to the first cleaning elements. In this embodiment, a cleaning liquid is not applied directly to the gripping surface, but, rather, indirectly. For this purpose, the cleaning liquid is applied to the first cleaning elements, which serve for the mechanical cleaning of the gripping surface, i.e., for example, a sponge, bristles, fingers, or knobs, such that the mechanical cleaning ultimately takes place wet and also comprises a chemical cleaning. At the same time, the first cleaning elements are also cleaned thereby.

In another embodiment, at least one such cleaning device can be designed to apply ultraviolet light to the gripping surface. In particular, application of UVA and/or UVB and/or UVC light is conceivable in this case.

In this connection, an embodiment can be particularly advantageous in which the gripping surface is equipped with photocatalysts, such as titanium oxides—in particular, titanium dioxide ($TiO_2$)—for example, in the form of a coating of the gripping surface. The UV light can now have a wavelength suitable for generating a photocatalytic self-cleaning on the gripping surface. This measure makes it possible to achieve an efficient microbacterial cleaning of the gripping surface. In combination with titanium oxides, a suitable wavelength may be in the region of 390 nm.

Another advantageous embodiment proposes that at least one such cleaning device be designed to apply a liquid or gaseous disinfectant to the gripping surface. As a result of the disinfection, in particular bacteria, fungi, and even viruses on the gripping surface can be killed. Preferably, such a cleaning device is used for disinfection in conjunction with a cleaning device for mechanical and/or chemical cleaning, but only, chronologically, after the mechanical or chemical cleaning.

Another advantageous embodiment proposes that at least one such cleaning device be designed for drying the gripping surface, such that it can also be referred to as a drying device. For example, such a cleaning device can be designed as a heating device in order to heat the steering device directly in the region of the gripping surface. This can take place, for example, by means of infrared rays. It is also conceivable that the cleaning device for drying the gripping surface generate a temperature-controlled air flow and thus act upon the gripping surface.

In another embodiment, the cleaning device can have at least one care device for applying a care product to the gripping surface. Depending upon the value of the vehicle, the gripping surface can consist of wood, leather, synthetic leather, or, generally, of plastic. The gripping surface can accordingly be subjected to greater or lesser stress by the cleaning. By using a care product, which can, for example, be a liquid, a paste, or a cream, the quality of the gripping surface can be permanently maintained. The care device can be equipped with corresponding care elements for applying the care product. For example, resilient care elements are also conceivable here, which can come into direct contact with the gripping surface, such as bristles, fingers, knobs, or a sponge. Here, too, it is conceivable to support the application of the care product in conjunction with a relative movement between the steering input unit and the cleaning box, or at least the respective care device or the respective care element.

Another advantageous embodiment provides that the cleaning box be designed to control the temperature of the region of the steering input unit arranged therein. For example, the steering input unit can be adapted to the temperature prevailing in the vehicle interior, at least in the region of the gripping surface. A cooling and/or a heating of the gripping surface is conceivable for this purpose. This can take place when the vehicle is stationary, and also during autonomous driving operation of the vehicle. For such a temperature control of the steering input unit in the box interior, the cleaning box can be connected, for example, to a channel system of an air conditioning system, and in particular to an HVAC system, wherein HVAC stands for heating, ventilation, and air conditioning. A temperature-controlled air flow of this vehicle air conditioning system or the HVAC system can thus be guided through the cleaning box, as a result of which the temperature-controlled air flow is applied to the steering input unit, at least in the region of the gripping surface.

The cleaning box can be formed, in its interior space, substantially like a negative form of the steering input unit, at least in the region of the gripping surface. In particular, the gripping elements provided for mechanical cleaning of the gripping surface can be arranged so as to be distributed along this negative form.

The cleaning device can also be equipped with a sensor system that detects contamination of the gripping surface. In this case, these can be sensors arranged directly in the gripping surface. Likewise, optical sensors are conceivable, which are arranged at a suitable location of the vehicle and scan the gripping surface. Furthermore, the cleaning device can be equipped with a controller that can carry out a cleaning process automatically. In this case, the controller can be coupled to a vehicle controller in order to identify, for example, an autonomous driving operation or another vehicle state that enables cleaning of the gripping surface.

It is understood that the features mentioned above and those still to be explained below can be used not only in the combination specified in each case, but also in other combinations or in isolation. Components, mentioned above and still to be mentioned in the following, of a superordinate unit, such as a device, an apparatus, or an arrangement, which are designated separately, can form separate parts or components of this unit or be integral regions or portions of this unit, even if this is shown differently in the drawings.

Preferred embodiments of the invention are illustrated in the drawings and are explained in more detail in the following description, wherein the same reference signs refer to identical or similar or functionally identical components.

BRIEF DESCRIPTION OF THE DRAWING FIGURES

In the drawings, schematically in each case.

DETAILED DESCRIPTION

Figure 1:
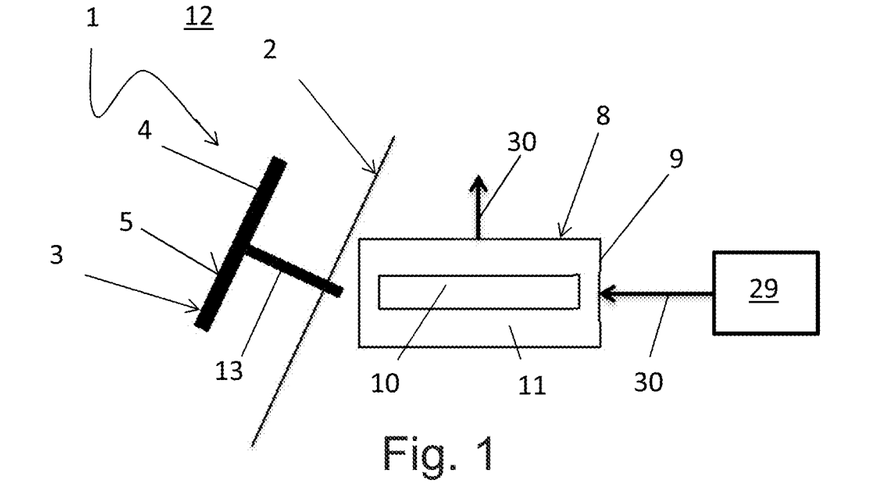
FIG. 1 is a greatly simplified schematic view of a vehicle having a steering device and a cleaning device, wherein a steering input unit is moved into a usage position.
Figure 2:
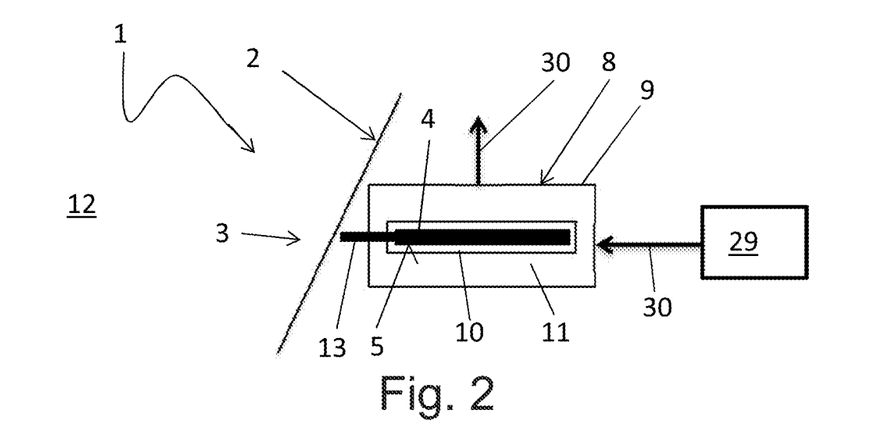
FIG. 2 shows a view as in FIG. 1, wherein the steering input unit is moved into a non-usage position.
Figure 8:
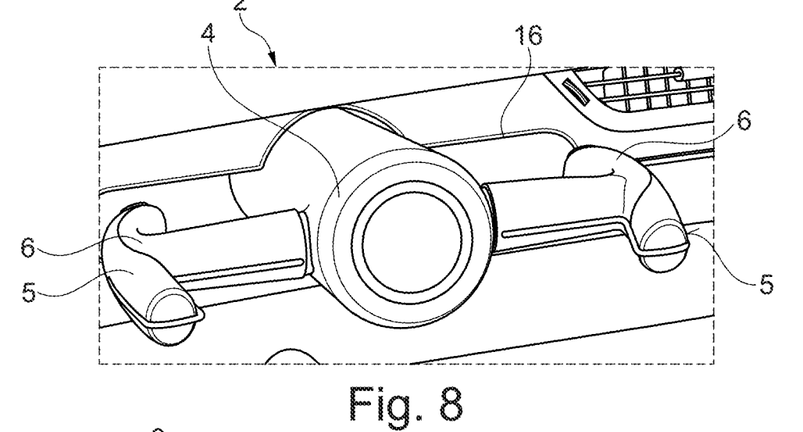
FIGS. 8 through 10 are simplified isometric views of the vehicle in the region of the steering input unit, in different positions.
Figure 9:
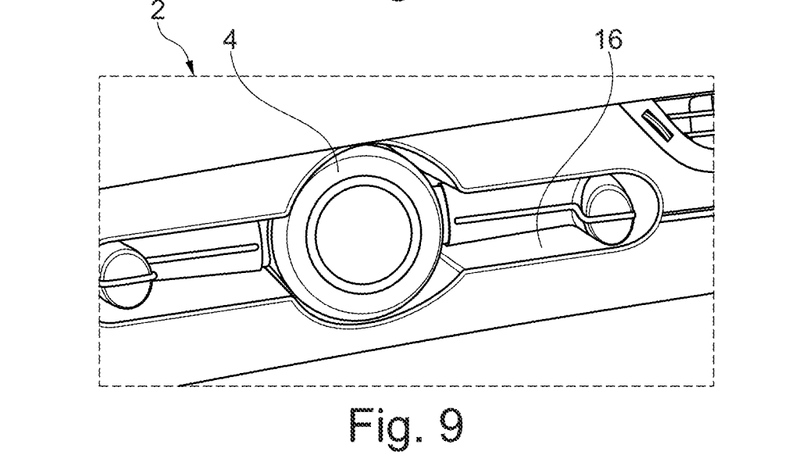
Figure 11:
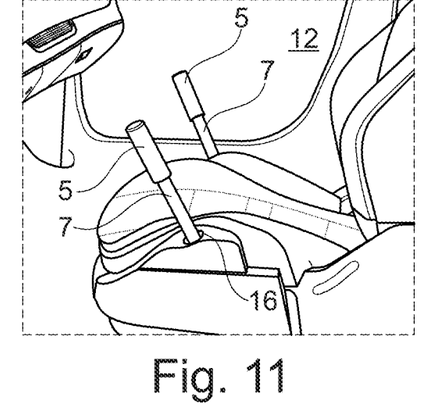
FIGS. 11 through 13 are views as in FIGS. 8 through 10, but in another steering input unit.
Figure 12:
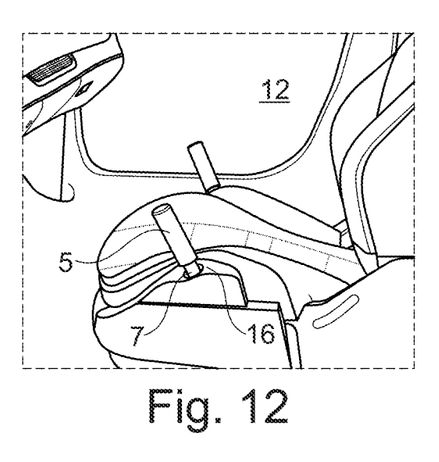
Figure 13:
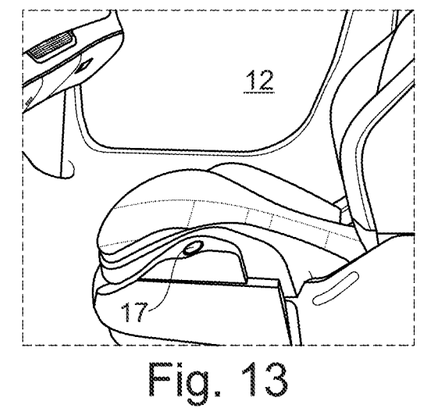

According to FIGS. 1 and 2, a vehicle 1, which is shown in a simplified section transverse to a dashboard 2, comprises a steering device 3 for steering the vehicle 1, which has a manually operable steering input unit 4, by means of which the vehicle driver can manually input steering commands into the steering device 3. For this purpose, the vehicle driver can manually grip the steering input unit 4. For this purpose, the steering input unit 4 has a one-piece or multi-piece gripping surface 5 that can be manually gripped by the vehicle driver for inputting steering commands into the steering device 3. In the example of FIGS. 1 and 2, the steering input unit 4 is designed as a steering wheel having a one-piece gripping surface 5 extending along the circumference. Purely by way of example, a different steering input unit 4, which has two gripping elements 6, is shown in FIGS. 8 and 9, but can otherwise be actuated like a steering wheel. In this case, the gripping surface 5 is multi-piece and distributed on the two gripping elements 6. Furthermore, FIGS. 11 through 13 show, purely by way of example, a steering input unit 4 which is formed having two steering rods 7. Here too, the gripping surface 5 is multi-piece and distributed on the two steering rods 7.

According to FIGS. 1 and 2, the vehicle 1 is also equipped with a cleaning device 8 for cleaning the gripping surface 5. The cleaning device 8 has a cleaning box 9 arranged on the vehicle 1 or in the dashboard 2 and enclosing a box interior 10, and having or containing at least one cleaning device 11, which is explained in more detail with reference to FIGS. 3 through 7. In the example of FIGS. 11 through 13, the cleaning device 8 has two cleaning boxes which are arranged next to a vehicle seat in a floor structure of a vehicle interior 12.

The steering input unit 4 is movable between a usage position shown in FIG. 1, in which it can be gripped by the vehicle driver, and a non-usage position shown in FIG. 2, in which it cannot be gripped by the vehicle driver. In the usage position, the steering input unit 4 according to FIG. 1 is located outside the cleaning box 9, wherein the steering input unit projects into the vehicle interior 12. According to FIG. 2, the steering input unit 4 is located in the cleaning box 9 in the non-usage position. For this purpose, a steering linkage 13, which connects the steering input unit 4 to the rest of the steering device 3, can be foldable, hinged, or telescopic, or can be designed to be adjustable in another suitable manner.

Figure 10:
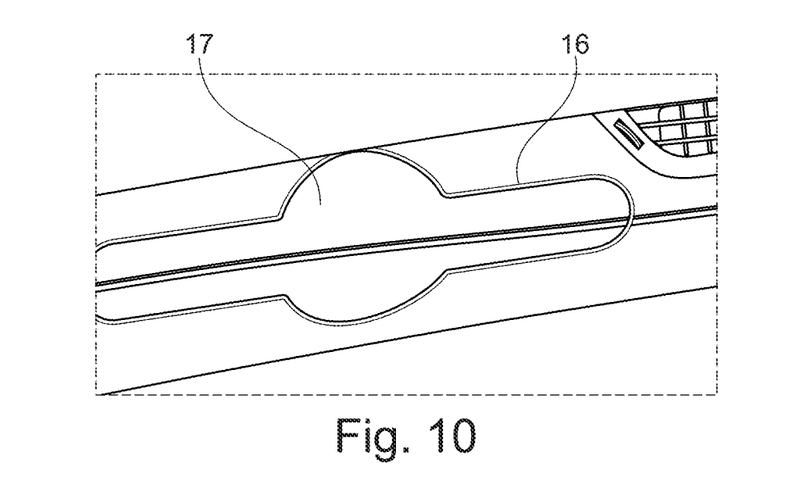

In its box interior 10, the cleaning box 9 is expediently designed as a negative form with respect to the relevant steering input unit 4. This can take place, for example, by means of the cleaning device 11 used in each case. Furthermore, it can expediently be provided that the cleaning box 9 be movable between an open state and a closed state. FIGS. 1 through 7, 10, and 13 each show a closed state, while FIGS. 8, 9, 11, and 12 show an open state. In the open state, the steering input unit 4 is movable between the usage position and the non-usage position. In the closed state, the steering input unit 4 is separated from the vehicle interior 12 when it is moved into the non-usage position. In the examples of FIGS. 3 through 7, for this purpose, the cleaning box 9 is designed in two parts, in such a way that it has an upper part 14 and a lower part 15 that are movable relative to one another, in order to enable the open state and the closed state. In contrast, in the examples of FIGS. 8 through 10 and 11 through 13, it is provided that the cleaning box 9 have an opening 16 through which the steering input unit 4 is movable between the vehicle interior 12 and the box interior 10. The cleaning box 9 is then, expediently, furthermore equipped with a cover 17 for closing this opening 16 in order to produce the closed state. In the example of FIG. 10, the cover 17 is arranged flush in the dashboard 2 in the closed state. In the example of FIGS. 11 through 13, the cover 17 is formed by a front end of the respective steering rod 7.

At least one cleaning device 11 can be designed for mechanically cleaning the gripping surface 5. According to FIG. 3, the cleaning device 11 can for this purpose have, for example, a resilient cleaning element 18, which comes into direct contact with the gripping surface 5 in order to mechanically clean the gripping surface. According to FIGS. 3 and 4, this cleaning element 18 can, for example, be a sponge. According to FIGS. 5 through 7, this cleaning element 18 can be a plurality of bristles or fingers or knobs.

Figure 3:
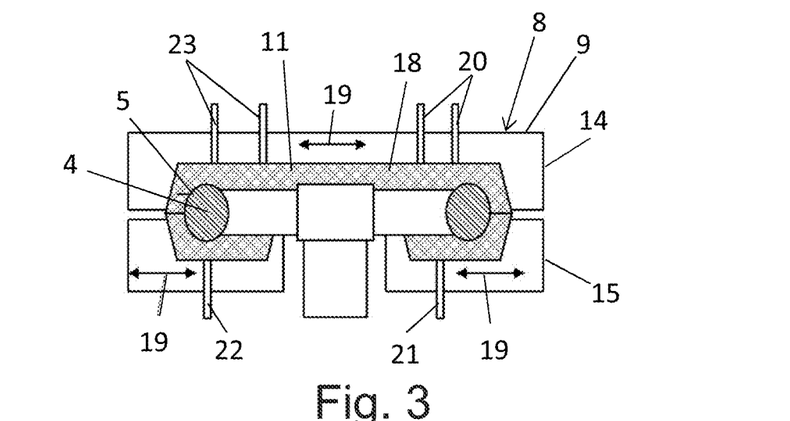
FIGS. 3 through 7 are each a greatly simplified sectional view through a cleaning box having different cleaning devices.

According to FIG. 3, the cleaning device 8 can be designed for generating a relative movement 19, indicated by double arrows, between the respective cleaning device 11 or the respective cleaning element 18 and the gripping surface 5. For example, the entire cleaning box 9 can be moved to produce the relative movement 19. Additionally, or alternatively, it is also conceivable to move the steering input unit 4 accordingly.

In the example of FIG. 3, the cleaning device 11 can additionally be designed such that a cleaning liquid can be applied to the gripping surface 5. FIG. 3 shows corresponding supply lines for supplying the cleaning liquid, and a drainage line 21 for discharging the cleaning liquid. In addition, the cleaning device 11 can also be designed to apply a liquid or gaseous disinfectant to the gripping surface 5. This can, for example, likewise be fed through the supply lines 20 and possibly discharged through the discharge line 21. Furthermore, this or another cleaning device 11 can be configured for drying the gripping surface 5. For example, a dried and/or heated air flow can be supplied to the box interior 10 via a further supply line 22, in order to dry the gripping surface 5. The exhaust air can be discharged via corresponding discharge lines 23.

Figure 4:
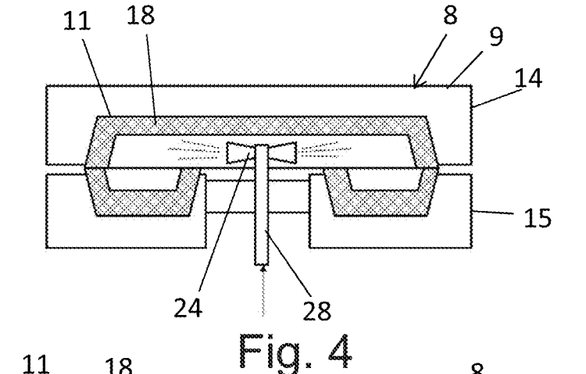

According to FIG. 4, it is also conceivable to design the respective cleaning device 11 in such a way that the first cleaning elements 18 provided for mechanical cleaning are subjected to a cleaning liquid with the aid of second cleaning elements 24, which expediently takes place before the steering input unit 4 is transferred into the cleaning box 9. The mechanical cleaning process can then be carried out wet, i.e., in conjunction with the cleaning liquid.

Figure 5:
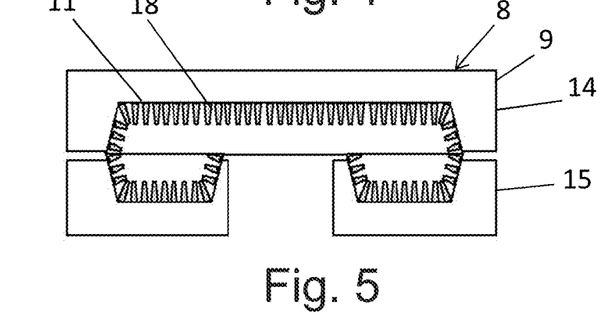
Figure 6:
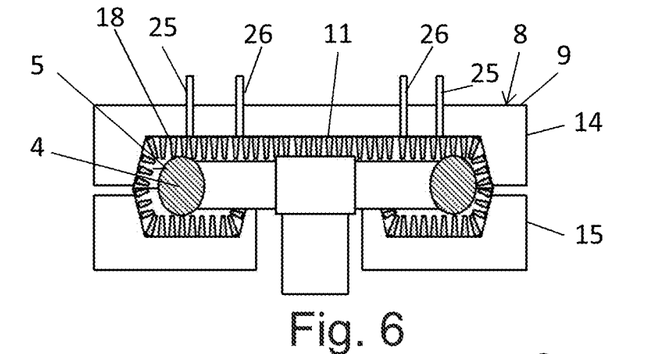
Figure 7:
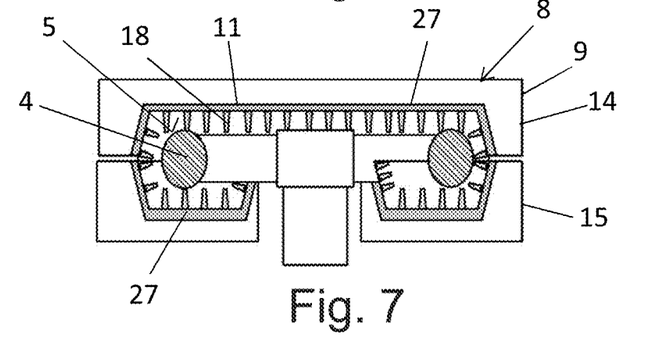

According to FIGS. 5 through 7, finger-like or knob-like cleaning elements 18 can be used for mechanically cleaning the gripping surface 5. A relative movement of these cleaning elements 18 relative to the gripping surface 5 can also be realized according to FIG. 6 by supplying compressed air—in particular, in a pulse-like manner—via supply lines 25, wherein it is possible for the compressed air to be discharged again via discharge lines 26.

According to FIG. 7, this or another cleaning device 11 can be configured for applying UV light to the gripping surface 5. For example, a corresponding UV light source 27, which allows for UV light irradiation of the gripping surface 5, can be arranged at a suitable location on an inner side, facing the box interior 10, of the cleaning box 9. In particular, the entire box interior 10 can be exposed to UV light, according to FIG. 7, such that UV irradiation of the cleaning elements 18 also takes place simultaneously. With the aid of UV light, a large number of microbacterial impurities can be killed.

Optionally, the gripping surface 5 can be equipped with photocatalysts—for example, in the form of an appropriate coating. The UV light can now be designed to produce a photocatalytic self-cleaning on the gripping surface 5, and accordingly have a wavelength suitable for this purpose. When titanium oxides are used as photocatalysts, a wavelength of 390 nm can be suitable, for example.

The cleaning device 8 can also have a care device 28, by means of which a care product can be applied to the gripping surface 5. According to FIG. 4, a nozzle or the like can, in principle, also be used for this purpose, which is also suitable for supplying a cleaning liquid. Preferably, separate systems are used here. For example, it is conceivable to apply the care product after the cleaning and after the disinfection of the gripping surface 5, as well as after the drying of the gripping surface 5. Subsequently, after the movement of the steering input unit 4 into its usage position, self-cleaning of the cleaning elements 18 can be carried out—for example, in order to free the latter from the care products again.

According to FIGS. 1 and 2, the cleaning box 9 can be designed for controlling the temperature of the steering input unit 4 arranged in the box interior 10. For example, the cleaning box 9 can be connected to an air conditioning system 29 for this purpose. For example, the cleaning box 9 can be integrated into a channel system 30 of the air conditioning system 29, such that air-conditioned air flowing in the channel system 30 flows through the box interior 9. Thus, the steering input unit 4 can be temperature-controlled, i.e., in particular, cooled or heated, as desired.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A vehicle, comprising:
   a steering device configured to steer the vehicle, wherein the steering device has a manually operable steering input unit configured to be manually gripped and to input steering commands, wherein the manually operable steering input unit has a one-piece or multi-piece gripping surface which is manually grippable by a vehicle driver to input steering commands; and
   an outer cleaning device configured to clean the gripping surface of the manually operable steering input unit, wherein
   the manually operable steering input unit is arranged on the vehicle so as to be movable between a usage position, in which the manually operable steering input unit is grippable by the vehicle driver, and a non-usage position in which the manually operable steering input unit cannot be gripped by the vehicle driver,
   the outer cleaning device has at least one cleaning box arranged on the vehicle, wherein the at least one cleaning box has or contains at least one inner cleaning device configured to clean the gripping surface,
   in the usage position at least a region of the gripping surface of the manually operable steering input unit is arranged outside the cleaning box, and
   in the non-usage position at least the region of the gripping surface of the manually operable steering input unit is arranged inside the cleaning box.

2. The vehicle of claim 1, wherein
   the manually operable steering input unit projects into a vehicle interior in the usage position, and
   the cleaning box is movable between an open state, in which the manually operable steering input unit is movable between the usage position and the non-usage position, and a closed state, in which the manually operable steering input unit moved into the non-usage position is separated from the vehicle interior.

3. The vehicle of claim 1, wherein the at least one inner cleaning device or the outer cleaning device is configured to manually clean the gripping surface.

4. The vehicle of claim 1, wherein the outer cleaning device is configured to generate a relative movement between the at least one inner cleaning device and the gripping surface.

5. The vehicle of claim 1, wherein
the at least one inner cleaning device or the outer cleaning device is configured to apply a cleaning liquid to the gripping surface, or
the at least one inner cleaning device or the outer cleaning device has first cleaning elements configured to mechanically clean the gripping surface and second cleaning elements configured to apply a cleaning liquid to the first cleaning elements.

6. The vehicle of claim 1, wherein the at least one inner cleaning device or the outer cleaning device is configured to apply UV light to the gripping surface.

7. The vehicle of claim 1, wherein the at least one inner cleaning device or the outer cleaning device is configured to apply a liquid or gaseous disinfectant to the gripping surface.

8. The vehicle of claim 1, wherein the at least one inner cleaning device or the outer cleaning device is configured to dry the gripping surface.

9. The vehicle of claim 1, wherein the outer cleaning device has at least one care device configured to apply a care product to the gripping surface.

10. The vehicle of claim 1, wherein the at least one cleaning box is configured to control a temperature of a region of the steering input unit arranged in the at least one cleaning box.

\* \* \* \* \*